United States Patent [19]

Bournonville et al.

[11] Patent Number: 5,215,950
[45] Date of Patent: Jun. 1, 1993

[54] CATALYST CONTAINING A ZEOLITE, A NOBLE METAL FROM THE FAMILY OF PLATINUM, AN ALKALI METAL OF AN ALKALINE EARTH METAL AND AN ADDITIONAL METAL, AS WELL AS THE USE THEREOF IN THE AROMATIZATION OF HYDROCARBONS CONTAINING 2 TO 4 CARBON ATOMS PER MOLECULE

[76] Inventors: Jean-Paul Bournonville, 43, rue des Groues Vauréal, 95000 Cergy Pontoise; Francis Raatz, 25, rue de la Carrière, 57500 Saint Avold; Bernard Juguin, deceased, late of Rueil Malmaison; by Jeannine Juguin, legal representative, 46, avenue du Stade, 92500 Rueil Malmaison; by Sylvie Juguin, legal representative, 1, Impasse des Buis, 31140 Aucamville, all of France

[21] Appl. No.: 704,153

[22] Filed: May 22, 1991

[30] Foreign Application Priority Data

May 23, 1990 [FR] France ................. 90 06557

[51] Int. Cl.$^5$ .................................. B01J 29/32

[52] U.S. Cl. ..................... 502/66; 502/71; 502/74

[58] Field of Search ................. 502/66, 71, 74

[56] References Cited

U.S. PATENT DOCUMENTS

| 4,727,206 | 2/1988 | Clayson et al. | 585/415 |
| 4,839,320 | 6/1989 | Trowbridge et al. | 502/66 |
| 4,861,740 | 8/1989 | Sachtler et al. | 502/66 |
| 4,923,835 | 5/1990 | Travers et al. | 502/66 |

FOREIGN PATENT DOCUMENTS 0361424 4/1990 European Pat. Off. .

Primary Examiner—Carl F. Dees

[57] ABSTRACT

The invention relates to a catalyst and a catalytic process for the aromatization of hydrocarbons containing 2 to 4 carbon atoms per molecule.

The catalyst contains a MFI zeolite and an amorphous matrix containing at least one noble metal from the platinum family, at least one additional metal chosen from tin, germanium, lead and indium and at least one alkali metal or alkaline earth metal.

12 Claims, No Drawings

CATALYST CONTAINING A ZEOLITE, A NOBLE METAL FROM THE FAMILY OF PLATINUM, AN ALKALI METAL OF AN ALKALINE EARTH METAL AND AN ADDITIONAL METAL, AS WELL AS THE USE THEREOF IN THE AROMATIZATION OF HYDROCARBONS CONTAINING 2 TO 4 CARBON ATOMS PER MOLECULE

BACKGROUND OF THE INVENTION

The present invention relates to a composite catalyst incorporating on the one hand a MFI structure zeolite containing silicon and aluminium and on the other hand a metal from the platinum group deposited on a refractory oxide support and to which are added at least one metal additive chosen from the group constituted by tin, germanium, indium and lead and at least one alkali metal or alkaline earth metal.

The invention also relates to the use of this composite catalyst in the aromatization reactions of hydrocarbons having 2 to 4 carbon atoms per molecule.

The aromatization reaction of propane and butane in the presence of a catalyst containing the zeolite ZSM5 (or MFI) and gallium was discovered and patented by British Petroleum (U.S. Pat. No. 4,175,057 and U.S. Pat. No. 4,180,689). Since this date other organizations and companies have filed patent applications concerning modifications of the solid (U.S. Pat. No. 4,795,844 European Patent EP-B-252,705) and/or to changes of the charge: $C_2$-$C_{12}$ fraction (European Patent EP-B-252,705), ethane and ethylene (European Patent EP-B-50,021 and U.S. Pat. No. 4,350,835). The method of introducing the gallium is also covered by patents (European Patents EP-B-120,018 and 184,927).

The addition of another metal to the system Ga-MFI has been envisaged for improving the aromatic selectivity and for reducing the coke quantity on the catalyst. Thus, the impregnation of a Ga/MFI catalyst by rhenium, associated with platinum or palladium makes it possible to significantly improve the aromatic production selectivity (U.S. Pat. No. 4,766,265). Other patents claim the addition of platinum and palladium to the Ga-MFI catalyst (U.S. Pat. No. 4,407,728, European Patents EP-B-215,579, 216,491, 224,162, 228,267 and Japanese Patents 61-268,634, 62-081,329, 61-2,277,636).

The addition of platinum to the MFI zeolite makes it possible to improve the propane conversion (T. INUI, F. OKAZUNI, Y. MAKINO, Chem. Express 1 (1), 53–56, 1985). However, the methane and ethane production selectivity is significantly improved. The addition of rhenium to the platinum further improves the production of methane and ethane by hydrogenolysis (S. ENGELS et al, Catalysis Today, 3, pp. 437–443, 1988). The addition of copper (P. MERIAUDEAU et al, Zeolites: Facts, Figures, Future, pp. 1423–1429, 1989) and chromium (E. S. SHPIRO et al, International Symposium on Zeolites as catalysts, Sorbents and Detergent builders, Wurzburg (GFR), p. 73, 1988) reduces methane production, but the aromatic selectivity remains inferior to Ga/MFI systems. Moreover, very recently the addition of sulphur to a Pt/MFI catalyst makes it possible to significantly improve its production selectivity to aromatics produced from paraffins containing 6 to 12 carbon atoms (U.S. Pat. No. 4,835,336).

SUMMARY OF THE INVENTION

It has been found that improved performance characteristics compared with what was known in the prior art can be obtained by aromatizing light hydrocarbons using a novel composite catalyst.

This catalyst comprises a MFI structure zeolite on the one hand and on the other hand a generally amorphous matrix or support, on which is deposited a noble metal from the platinum family and at least one additional metal chosen from the group of tin, germanium, lead and indium, said support also containing at least one alkali metal or at least one alkaline earth metal chosen from the group of lithium, sodium, potassium, rubidium, cesium, barium, calcium, beryllium, magnesium and strontium.

The MFI structure zeolite constituting part of the catalyst of the present invention can be prepared by all known procedures. The synthesis of said MFI zeolite can be carried out in a standard OH$^-$ medium, in the presence or absence of organic structuring agents and/or alcohol. The synthesis of the MFI zeolite in the OH$^-$ medium in accordance with prior art procedures is described in Synthesis of High Silica Zeolites, P. Jacobs and J. Martens, Studies in Surface Science and Catalysis, Vol. 33, Elsevier editor, 1987. The zeolite MFI can also be synthesized in less conventional media, such as e.g. the fluoride medium (European Patent EP-A-172,068).

After synthesis, the MFI zeolite is transformed into hydrogen form by the partial or total elimination of the organic compounds and/or alkali metal or alkaline earth cations contained therein, optionally following synthesis. All prior art procedures can be used for obtaining the hydrogen form, such as e.g. calcinations under an oxidizing or non-oxidizing atmosphere, ion exchanges optionally followed by calcination, various chemical treatments, etc.

All MFI zeolites synthesized in the system Si-Al are suitable for the present invention. However, their Si/Al ratio is to be higher than 7, preferably higher than 25 and more particularly between 40 and 200.

The supports of the metals added to the zeolite are generally chosen from among oxides of metals of groups II, III and/or IV of the periodic classification of elements, such as e.g. magnesium, aluminium, titanium, zirconium, thorium or silicon oxides, taken singly or mixed with one another or with oxides of other elements of the periodic classification, such as e.g. boron. It is also possible to use carbon.

The preferred support is alumina. The specific surface of alumina can advantageously be between 50 and 600 m$^2$/g, preferably between 150 and 400 m$^2$/g.

The composite catalyst according to the present invention can be prepared by two methods, whose principles are given below.

First method: This method involves mixing the MFI zeolite with the suppot. This mixture can take place between two powders, between two shaped solids, between a powder and one of the shaped solids. It is also possible to jointly shape the two solids by all prior art procedures, such as pelletizing, extrusion, dragee formation, droplet coagulation and drying by atomization. During these shaping operations, if necessary, it is possible to add a shaping additive (silica, etc.). After mixing and/or shaping, deposition takes place of the various active agents on the support (i.e. in the presence of the zeolite).

Second method: In the method, the active agents are deposited on the support beforehand and it is mixed or shaped with the MFI zeolite under the same conditions as previously. In a variant, the zeolite could be introduced into the composite catalyst at any random one of the deposition stages of the active agents on the support.

The preferred preparation method consists of depositing the active agents on the support, followed by the introduction of the zeolite into the final catalyst by shaping two powders. Shaping preferably takes place by micron milling or grinding and this can be carried out by using the wet grinding method.

The composite catalyst contains between 1 and 99% by weight zeolite, the residue totalling 100% being constituted by the support filled or charged with different active agents. The respective zeolite and support proportion varies within a wide range, because it is dependent on the one hand on the Si/Al ratio of the zeolite and on the other on the content of active agents of the support.

The portion of the composite catalyst incorporating the noble metal is generally prepared according to conventional methods consisting of impregnating the support by means of solutions of compounds of metals to be introduced. Use is made either of a common solution of these metals, or of separate solutions for the metals of the platinum group and for the additional metal or metals. When using several solutions, intermediate drying and/or calcination operations can be carried out. The final stage is normally calcination, e.g. at between approximately 500 and 1000, preferably in the presence of free oxygen, e.g., with air scavenging.

The platinum (and optionally another noble metal from the platinum group) can be incorporated into the support by impregnating the latter with the aid of an adequate aqueous or non-aqueous solution containing a salt or a compound of the noble metal. The platinum is generally introduced into the support in the form of chloroplatinic acid, but it is also possible to use compounds such as ammonium chloroplatinate, dicarbonyl platinum dichloride, hexahydroxyplatinic acid, palladium chloride and palladium nitrate.

The element chosen from by tin, germanium, lead and indium can be introduced via compounds such as, e.g., tin nitrate, bromides and chlorides, lead carbonate, acetate, nitrate and halides, germanium oxalate and chloride or indium chloride or nitrate.

The element chosen from the group constituted by alkali metals and alkaline earth metals can be introduced via compounds such as halides, nitrates, carbonates, cyanides and oxalates.

A production process comprises the following stages:
a) introduction onto the support of at least one element chosen from alkali metals and alkaline earth metals,
b) calcination of the product obtained in stage a),
c) introduction onto the support of at least one noble metal from the platinum family, in the form of at least one halogen compound of said metal,
d) calcination of the product obtained in stage c),
e) introduction onto the product obtained in stage b) of at least one additional metal in the form of at least one organometallic compound of the said metal M.

Among the compounds of the metal or metals from the platinum group which can be used in the present invention, reference is made to ammoniated complexes in an exemplified manner.

In particular in the case of platinum, reference is made to hexamine platinum IV salts of formula $(Pt(NH_3)_6)X_4$, in which X is a halogen atom chosen from the group formed by fluorine, bromine and iodine and preferably X is a chlorine atom; halogenopentamine platinum IV salts of formula $(Pt\ X(NH_3)_5)X_3$; and tetrahalogenodiamine platinum IV salts of formula $Pt\ X_4(NH_3)_2$, in which X has the meaning given hereinbefore; as well as platinum complexes with halogens, polyketones and halogenated polyketone compounds of formula $H(Pt(aca)_2X)$ in which X has the meaning given hereinbefore and aca represents the remainder of the formula $C_5H_7O_2$ derived from acetyl acetone.

The introduction of the noble metal from the platinum group is preferably carried out by impregnation with the aid of an aqueous or organic solution of one of the aforementioned organometallic compounds. Among the organic solvents which can be used, reference is made to paraffinic, naphthenic or aromatic hydrocarbons and halogenated organic compounds having e.g. 1 to 12 carbon atoms in their molecule. Particular reference is made to n-heptane, methyl cyclohexane, toluene and chloroform. It is also possible to use mixtures of solvents.

The supports are conventional supports of the types defined hereinbefore and e.g. containing an alkali metal or alkaline earth metal.

Following the introduction of the noble metal from the platinum group, the product obtained is optionally dried and calcined preferably at a temperature of approximately 400° to 1000° C.

Following said calcination, the additional metal or metals are introduced. Before introducing the said metal M high temperature hydrogen reduction optionally takes place at e.g. 300° to 500° C. This reduction can e.g., involve a slow increase of temperature under hydrogen flow up to the maximum reduction temperature, which is, e.g., between 300° and 500° C., and preferably between 350° and 450° C., and then maintaining under oxygen continues for 1 to 6 hours at this temperature.

The additional metal M can be introduced before or after noble metal introduction. If it is introduced before the noble metal, the compound used will be chosen from halides, nitrates, acetates, carbonates and oxalates of the additional metal. Introduction advantageously takes place in an aqueous solution. In this case, prior to the introduction of the noble metal, calcination is performed under air at a temperature between 400° and 1000° C.

The additional metal M can be introduced after noble metal introduction in the form of at least one organic compound chosen from complexes and in particular polyketone complexes of metals M and hydrocarbyl metals such as metal alkyls, cycloalkyls, aryls, alkylaryls and aryl alkyls.

The metal M is advantageously introduced with the aid of a solution in an organic solvent of the organometallic compound of the said metal M. It is also possible to use organohalogenated compounds of the metals M. Among the compounds of metals M particular reference is made to tetrabutyl tin, tetramethyl tin, tetrapropyl germanium, tetraethyl lead, indium acetyl acetonate and triphenyl indium.

The impregnation solvent is chosen from paraffinic, naphthenic or aromatic hydrocarbons containing 6 to 12 carbon atoms per molecule and halogenated organic compounds containing 1 to 12 carbon atoms per molecule. Reference is made to n-heptane, methyl cyclohexane, toluene and chloroform. It is possible to use mixtures of the aforementioned solvents.

This method of introducing the metal M has already been described in U.S. Pat. No. 4,548,918. However, the combination of the introduction method of the metal from the platinum group and the introduction method of the metal M produces a particular synergy.

The part of the composite catalyst containing the noble metal contains by weight, based on the support (a), approximately 0.01 to 2% and more particularly approximately 0.1 to 0.5% of at least one noble metal from the platinum group, (b) approximately 0.005 to 0.60% and preferably 0.01 to 0.50% tin or 0.005 to 0.70% and preferably approximately 0.01 to 0.6% and more particularly 0.02 to 0.50% of at least one metal chosen from germanium, lead and indium, (c) approximately 0.01 to 2% and more particularly approximately 0.1 to 0.6% of at least one metal chosen from alkali metals and alkaline earth metals and preferably lithium and potassium and mixtures thereof.

When there are at least two metals from the tin, germanium, lead and indium group, the total content of metals of this group is approximately 0.02 to 1.20% and preferably 0.02 to 1.0% and more specifically 0.03 to 0.80%.

In the process according to the invention, at the end of the preparation of that part of the composite catalyst which contains the noble metal, the latter is generally calcined at between 450° and 1000° C. but, following the calcination, the catalyst advantageously undergoes an activation treatment under hydrogen and at high temperature, e.g. 300° to 500° C., in order to obtain a more active metal phase. The procedure of this treatment under hydrogen e.g. consists of a slow temperature increase under hydrogen flow up to the maximum reduction temperature, which is e.g. between 300° and 500° C. and preferably between 350° and 450° C., followed by maintenance at this temperature for 1 to 6 hours.

This catalyst preparation procedure leads to a solid in which the metals are homogeneously distributed throughout the volume of the catalyst grain and are in a metallic state following the reduction treatment under hydrogen scavenging at between 300° and 500° C. and maintaining for 1 to 6 hours under hydrogen at the chosen final temperature.

For example, a particular method for the preparation of catalysts involves performing the following stages:
(a) an alumina support is impregnated with an aqueous lithium nitrate solution,
(b) the product obtained in stage (a) is dried,
(c) the product obtained in stage (b) is calcined,
(d) the product obtained in stage (c) is impregnated by an aqueous solution of a compound of a metal chosen from tin, germanium, indium and lead,
(e) the product obtained in stage (d) is dried,
(f) the product obtained in stage (e) is calcined,
(g) the product obtained in stage (f) is impregnated by a platinum acetyl acetonate solution in toluene,
(h) the product obtained in stage (g) is dried,
(i) the product obtained in stage (h) is calcined and
(j) the product obtained in stage (i) is reduced under hydrogen flow.

Another advantageous method for the preparation of catalysts can be carried out as follows:
(a) an alumina support is impregnated with an aqueous lithium nitrate solution,
(b) the product obtained in stage (a) is dried,
(c) the product obtained in stage (b) is calcined,
(d) the product obtained in stage (c) is impregnated with an ammoniacal tetraamine platinum chloride solution,
(e) the product obtained in stage (d) is dried,
(f) the dry product obtained in stage (e) is calcined,
(g) the product obtained in stage (f) is reduced under hydrogen flow,
(h) the product obtained in stage (g) is contacted with a hydrocarbon solvent and with said organic compound of said metal M, e.g. by immersing the material in a hydrocarbon solvent already containing the organic compound or by immersing the material in a hydrocarbon solvent and then injecting into the mixture obtained a solution of the organic compound of said metal M in a hydrocarbon solvent and, e.g., that in which the said material has been immersed and
(i) the product obtained in stage (h) is reduced under hydrogen flow.

The following examples illustrate the invention without limiting the scope thereof.

EXAMPLE 1

The aim is to transform propane in the presence of a catalyst based on a mixture of a MFI zeolite with a ratio of Si/Al=45 and an alumina containing platinum, a metal chosen from tin, germanium, indium and lead and lithium and/or potassium.

Preparation of the MFI zeolite:

The MFI zeolite is synthesized in the presence of an organic structuring agent using one of the formulations known from the prior art U.S. Pat. No. 3,702,886. This zeolite is transformed into a H form by the following treatments:

calcination under an air-nitrogen mixture (10% oxygen in the mixture) at 550° C. and for 4 hours, three exchanges in 5N $NH_4NO_3$ at 100° C. and calcination in air at 530° C., for 5 hours and with a flow rate of 5 l/h/g.

The Si/Al ratio of the HMFI zeolite is 45, its pore volume measured by nitrogen adsorption at 77 K exceeds 0.160 $cm^3/g$.

Preparation of the alumina containing the chosen metals:

Preparation of an alumina A containing 0.30% by weight platinum.

The alumina A is prepared by adding to 100 g of alumina (specific surface 240 $m^2/g$ and pore volume 0.58 $cm^3/g$) 100 cc of a platinum acetyl acetonate solution in toluene. The platinum concentration of this solution is 3 g/l.

It is left in contact for 6 hours, followed by suction filtering, drying for 1 hour at 100° to 120° C. and then calcining for 2 hours at 530° C. It is then reduced under a dry nitrogen stream for 2 hours at 450° C.

In the same way, preparation takes place of two aluminas A' and A" respectively containing 0.60 and 1.1% by weight platinum.

Preparation of an alumina B (comparative) containing 0.30% by weight platinum and 0.50% by weight lithium.

The product (B) (comparative) is prepared by adding to 100 g of alumina support 100 cc of an aqueous lithium nitrate solution. Contacting takes place for 6 hours, followed by suction filtering, drying for 1 hour at 100° to 120° C. and then calcining for 2 hours at 530° C.

On the lithium-containing calcined product, platinum impregnation takes place in the same way as for product (A).

Preparation of an alumina C containing (by weight) 0.3% platinum, 0.3% tin and 0.5% lithium.

After fixing the lithium in accordance with the same procedure as adopted for product (B), an aqueous tin acetate solution is contacted with the alumina support at a rate of 100 cc of solution per 100 g of support for 6 hours. The solid obtained is then suction filtered and dried for 1 hour at 100° to 120° C. and then calcined at 530° C.

The platinum is then impregnated on the calcined solid containing lithium and tin adopting the same procedure as for product A.

Preparation of an alumina D containing (by weight) 0.3% platinum, 0.3% germanium and 0.5% lithium.

The preparation procedure for product D is strictly identical to that for product C, except that use is made of germanium oxalate in place of tin acetate.

Preparation of an alumina E containing (by weight) 0.3% platinum, 0.3% lead 0.5% lithium.

The preparation procedure for product E is strictly identical to that for product C, except that the tin acetate is replaced by lead acetate.

Preparation of an alumina F containing (by weight) 0.3% platinum, 0.3% indium and 0.5% lithium.

The preparation procedure for catalyst F is identical to that for catalyst C, except that the tin acetate is replaced by indium nitrate.

Preparation of an alumina G containing (by weight) 0.3% platinum, 0.3% tin and 0.5% lithium.

Product B is reduced under a hydrogen stream for 2 hours at 450° C. and 100 g of this catalyst are immersed in 300 cc of n-heptane. Into the n-heptane containing the catalyst are then injected 3 g of a tetra-n-butyl tin solution in n-heptane (10% tin). Contact between the platinum catalyst and the tetra n-butyl tin solution is maintained for 6 hours at the heptane reflux temperature. The impregnation solution is then discharged and three washing operations take place with pure n-heptane at the n-heptane reflux temperature. The catalyst is then dried and can then undergo either calcination under air for 2 hours at 500° C., followed by reduction under a nitrogen stream at 450° C. for 2 hours before being introduced into the reactor, or can directly undergo reduction under a nitrogen stream at 450° C. for 2 hours before being introduced into the reactor.

Preparation of an alumina H containing (by weight) 0.30% platinum and 0.30% tin (comparative alumina).

The catalyst H is prepared by adding to 100 g of alumina 100 cc of a platinum acetyl acetonate solution in toluene. The platinum concentration of this solution is 9 g/l. Contacting takes place for 6 hours, followed by suction filtering, drying for 1 hour at 120° C. and calcining for 2 hours at 530° C. under dry air.

The tin is then fixed in accordance with the procedure described for the preparation of product C.

Preparation of a catalyst I: preparation takes place of a catalyst similar to and prepared in accordance with catalyst C, but which also contains germanium introduced into the catalytic material in the manner indicated for catalyst D. The catalyst I contains 0.15% germanium and 0.15% tin.

EXAMPLE 2

The aluminas prepared hereinbefore were tested either alone or mixed with the MFI zeolite prepared in the manner described hereinbefore. The zeolite was also tested alone. These products underwent a propane transformation test under the following conditions:

| temperature | 450° C. |
|---|---|
| pressure | atmospheric |
| pph | 0.5 h$^{-1}$ |
| charge | $C_3H_8$ |

Testing firstly took place of the two solids, the MFI zeolite and the catalyst C, both alone and in mixture. The results are given below after 2 hours reaction.

TABLE I

| Catalyst | Conversion (molar %) | Selectivity (molar %) | | | | |
|---|---|---|---|---|---|---|
| | | $CH_4$ | $C_2H_6$ | $C_2H_4$ | $C_3H_6$ | Aromatics |
| MFI zeolite (comparative) | 14 | 45 (26.6) | 15 (16.6) | 10 (10.3) | 30 (46.5) | 0 |
| Catalyst C (Pt + Sn + Li/alumina) | 20 | 5 (2) | 5 (3.7) | 0 | 90 (94.3) | 0 |
| Mixture (50% zeolite 50% catalyst C) | 50 | 15 (6.0) | 30 (22.3) | 10 (6.9) | 25 (26.1) | 20 (38.7) |
| Mixture (25% zeolite 75% catalyst C) | 25 | 5 (1.5) | 15 (8.6) | 5 (2.7) | 35 (27.9) | 40 (59.3) |
| Mixture (10% zeolite 90% catalyst C) | 18 | 5 (1.7) | 10 (6.4) | 0 | 65 (58.5) | 20 (33.4) |

*NB: The bracketed figures are the weights obtained, based solely on $C_6H_6$ for the aromatics.

Whereas the zeolite alone produces more than 50% light gases ($CH_4$ and $C_2H_8$) and the catalyst C only produces propylene, the association of the two solids makes it possible to significantly increase the production selectivity of the aromatics.

EXAMPLE 3

(comparative)

Table II gives the conversions and selectivities obtained with MFI alone and mixtures of MFI with successively solid A, which contains alumina and 0.30% by weight platinum, solid A', in which the platinum content is 0.6% by weight, solid A" in which the platinum content is 1.1% by weight and solid H, which contains alumina and 0.3% by weight platinum and 0.3% by weight tin.

TABLE II

| Catalyst | Conversion (molar %) | Selectivity (molar %) | | | | |
|---|---|---|---|---|---|---|
| | | $CH_4$ | $C_2H_6$ | $C_2H_4$ | $C_3H_6$ | Aromatics |
| MFI | 14 | 45 | 15 | 10 | 30 | 0 |
| Mixture 25% MFI + 75% A | 15 | 35 | 30 | 5 | 20 | 10 |
| Mixture 25% MFI + 75 A' | 18 | 33 | 30 | 5 | 20 | 12 |
| Mixture 25% MFI + 75% A" | 17 | 34 | 30 | 5 | 20 | 11 |
| Mixture 25% MFI + 75% H | 20 | 7 | 18 | 5 | 40 | 30 |

EXAMPLE 4

25% by weight MFI zeolite with a Si/Al ratio of 45 prepared in accordance with Example 1 were mixed with 75% by weight catalyst A (comparative), B (comparative) and C respectively. The results are given in the following table III.

TABLE III

| Catalyst | Conversion (molar %) | Selectivity (molar %) | | | | |
|---|---|---|---|---|---|---|
| | | CH$_4$ | C$_2$H$_6$ | C$_2$H$_4$ | C$_3$H$_8$ | Aromatics |
| MFI zeolite + Catalyst A platinum/alumina | 15 | 35 | 30 | 5 | 20 | 10 |
| MFI zeolite + catalyst B platinum + lithium/alumina | 30 | 35 | 40 | 5 | 10 | 10 |
| MFI zeolite + catalyst C Pt + Sn + Li/alumina | 25 | 5 | 15 | 5 | 35 | 40 |

The values are given after 2 hours reaction. The addition of catalyst A does not improve the performance characteristics in the sense of the activity and the selectivity. The addition of catalyst B improves the activity, but not the selectivity. Catalyst C according to the invention gives a good selectivity of aromatic products.

EXAMPLE 5

This examples uses a MFI zeolite of Si/Al ratio 36 and synthesized in the absence of the organic compound in accordance with a synthesis procedure described in "Studies in Surface Science and Catalysis", Vol. 33, 1987, p. 134. After synthesis, the zeolite underwent the following treatments:

three exchanges in NH$_4$NO$_3$ at 10° to 100° C. for 6 hours, calcination in air at 550° C., for 4 hours and a flow rate of 31/h/g and 25% by weight MFI zeolite of Si/Al ratio 36 were mixed with 75% by weight of catalysts C,D,E,F and G respectively.

The results obtained under the aforementioned operating conditions are given in the following Table IV.

The nature of the MFI is not critical, because the MFI-catalyst C mixtures in Tables III and IV lead to the same results.

TABLE IV

| Catalyst | Conversion (molar %) | Selectivity (molar %) | | | | |
|---|---|---|---|---|---|---|
| | | CH$_4$ | C$_2$H$_6$ | C$_2$H$_4$ | C$_3$H$_8$ | Aromatics |
| MFI zeolite + catalyst C (Pt + Sn + Li) | 25 | 5 | 15 | 5 | 35 | 40 |
| MFI zeolite + catalyst D (Pt + Ge + Li) | 23 | 6 | 14 | 5 | 37 | 38 |
| MFI zeolite + catalyst E (Pt + Pb + Li) | 24 | 7 | 14 | 6 | 34 | 39 |
| MFI zeolite + catalyst F (Pt + In + Li) | 22 | 7 | 13 | 5 | 38 | 37 |
| MFI zeolite + catalyst G (Pt + Sn + Li) | 28 | 4 | 13 | 5 | 35 | 43 |
| MFI zeolite + catalyst I (Pt + Sn + Ge + Li) | 29 | 4 | 12 | 5 | 34 | 45 |

We claim:

1. A catalyst comprising (a) a MFI zeolite, (b) a matrix containing at least one noble metal from the platinum group, at least one additional metal which is tin, germanium, lead or indium and at least one alkali metal or alkaline earth metal.

2. A catalyst according to claim 1, containing by weight:
   (a) 1 to 99% MFI zeolite and
   (b) 99 to 1% of a matrix containing 0.01 to 2% of a metal from the platinum group, 0.005 to 0.60% of said additional metal when the latter is tin or 0.005 to 0.70% of said additional metal when the latter is germanium, lead or indium and 0.01 to 2% of at least one alkali metal or alkaline earth metal.

3. A catalyst according to claim 1, wherein the matrix is alumina.

4. A catalyst according to claim 1 wherein the matrix contains, by weight, 0.1 to 0.5% of at least one noble metal from the platinum group, 0.01 to 0.5% tin or 0.01 to 0.6% germanium, tin or lead and 0.1 to 0.6% of at least one alkali metal or alkaline earth metal.

5. A catalyst according to claim 1 containing as said additional metal tin and germanium or lead, the total additional metal content being between 0.02 and 1.20%.

6. A catalyst according to claim 1 containing a matrix of alumina, platinum, and lithium or potassium.

7. A catalyst according to claim 1, wherein said additional metal comprises tin.

8. A catalyst according to claim 2, wherein said additional metal comprises tin.

9. A catalyst according to claim 3, wherein said additional metal comprises tin.

10. A catalyst according to claim 4, wherein said additional metal comprises tin.

11. A catalyst comprising a component (a) consisting essentially of a MFI zeolite, and a component (b) comprising a matrix containing at least one noble metal from the platinum group, at least one additional metal which is tin, germanium, lead or indium and at least one alkali metal or alkaline earth metal.

12. A catalyst comprising a component (a) consisting of a MFI zeolite, and a component (b) comprising a matrix containing at least one noble metal from the platinum group, at least one additional metal which is tin, germanium, lead or indium and at least one alkali metal or alkaline earth metal.

* * * * *